US006914675B1

(12) United States Patent
Drevillon

(10) Patent No.: US 6,914,675 B1
(45) Date of Patent: Jul. 5, 2005

(54) ELLIPSOMETRIC METHOD AND CONTROL DEVICE FOR MAKING A THIN-LAYERED COMPONENT

(75) Inventor: Bernard Drevillon, Clamart (FR)

(73) Assignee: Centre National de la Recherche Scientifique, Paris Cedex (FR)

(*) Notice: Subject to any disclaimer, the term of this patent is extended or adjusted under 35 U.S.C. 154(b) by 0 days.

(21) Appl. No.: 09/719,825

(22) PCT Filed: Jun. 11, 1999

(86) PCT No.: PCT/FR99/01394

§ 371 (c)(1),
(2), (4) Date: Jun. 25, 2001

(87) PCT Pub. No.: WO99/66286

PCT Pub. Date: Dec. 23, 1999

(30) Foreign Application Priority Data

Jun. 16, 1998 (FR) .............................. 98 07594

(51) Int. Cl.[7] ................................................ G01J 4/00
(52) U.S. Cl. ...................................................... 356/369
(58) Field of Search ....................... 438/3, 5–18; 356/31, 356/364–370, 5; 430/30, 5; 250/225

(56) References Cited

U.S. PATENT DOCUMENTS 4,941,138 A * 7/1990 Chida et al.
5,131,752 A * 7/1992 Yu et al. ...................... 356/369
5,277,747 A * 1/1994 Aspnes ........................ 156/626
5,666,200 A * 9/1997 Drevillon et al. ........... 356/368
5,822,035 A * 10/1998 Bille ........................... 351/215
6,002,485 A * 12/1999 Masao ......................... 356/369
6,052,188 A * 4/2000 Fluckiger et al. ........... 356/369
6,081,334 A * 6/2000 Grimbergen ................. 356/357
6,128,084 A * 10/2000 Nanbu et al. ................ 356/369
6,175,412 B1 * 1/2001 Drevillion et al. .......... 356/369
6,384,916 B1 * 5/2002 Furtak ......................... 356/369
6,391,690 B2 * 5/2002 Miyasaka .................... 438/149
6,485,872 B1 * 11/2002 Rosenthal et al. ............ 430/30

FOREIGN PATENT DOCUMENTS

FR          2 731 074         8/1996

* cited by examiner

Primary Examiner—Zandra V. Smith
(74) Attorney, Agent, or Firm—Young & Thompson

(57) ABSTRACT

A method for controlling the production of an object controlled by a gas panel, by performing an ellipsometric measurement on the object represented by its Mueller matrix; controlling, with a gas panel, the manufacture on the basis of the ellipsometric measurement. Certain parameters of the Mueller matrix are determined in advance, for characterizing the manufacture, and only these parameters are extracted from the ellipsometric measurement during manufacture, the parameters being two different parameters of the ellipsometric angles $\psi$ and $\Delta$ and trigonometric functions thereof.

18 Claims, 2 Drawing Sheets

ELLIPSOMETRIC METHOD AND CONTROL DEVICE FOR MAKING A THIN-LAYERED COMPONENT

BACKGROUND OF THE INVENTION

This invention relates to a method of and a control device for making a thin-layered component. This operation is performed preferably out of gas dissociation.

DESCRIPTION OF THE RELATED ART

Such processes and devices, used in particular for making solid-state components, are already known. Numerous solid-state components imply depositing layers, often numerous layers, on a substrate, whose composition and thickness are essential to ensure quality of the products made.

Real-time processes for ellipsometric control of these layers during manufacture have already been suggested and implemented. Until now, implemented ellipsometric measurements use simplified ellipsometry, also called conventional ellipsometry, and aim at measuring the characteristic 'parameters $\Psi$ and $\Delta$' of the sample. The surface of the object constitutes a system, it is lit by a luminous beam that is reflected and the polarisation state of the reflected beam (that may be transmitted) is compared to that of the incident beam. The variation of the polarisation vector is described from reflection coefficients $R_s$ and $R_p$, respectively perpendicular and parallel to the plane of incidence ($R_s$ and $R_p$ are complex amplitudes).

The system is then characterised generally by the angles $\Psi$ and $\Delta$ that are connected to the ratios ($R_p/R_s$) by the relation:

$$tg\Psi.\exp(i\Delta)=(Rp/R_s)$$

These conventional ellipsometric methods have been enhanced regularly. It can be referred, for instance, to the European patent EP-0.663.590 that concerns a modulated spectroscopic ellipsometer. They prove satisfactory when measuring isotropic layers with plane interfaces.

Still, in numerous cases, it has been shown that these measurements are insufficient to characterise a manufacturing process. In particular when the system is anisotropic, couplings may be observed among the polarisation modes.

This Is due to the fact that the Jones matrix representing the parameters taken into account generally in conventional ellipsometry with the following shape $$\begin{bmatrix} R_p & R_{ps} \\ R_{sp} & R_s \end{bmatrix}$$

$R_{ps}$, $R_{sp}$ are nil when the system is anisotropic and one of them at least is not when the system is anisotropic. Consequently, an anisotropic system is characterised insufficiently by the ratio $R_p/R_s$.

The Mueller ellipsometry is known more generally. It is based on the observation that the polarimetric state of a luminous flux is represented completely by a dimension 4 vector, called Stokes vector $$\begin{bmatrix} i \\ u \\ v \\ w \end{bmatrix}$$

and that modifications, introduced by a system, are represented by a matrix, so-called the Mueller matrix, of dimension 4×4 with therefore 16 coefficients.

Methods and devices aiming at measuring the 16 coefficients of the Mueller matrix enable characterisation of a system generally. Still, it can be easily understood that the extraction of 16 parameters during ellipsometric measurements implies resorting to sophisticated devices and heavy data processing, thereby calling for expensive devices and for processes that are often relatively slow. So far, these devices, too slow and too heavy, could not be used for real-time control of manufacturing or preparing methods.

The Mueller matrix being represented generally as follows:

$$M = \begin{bmatrix} m_{00} & m_{01} & m_{02} & m_{03} \\ m_{10} & m_{11} & m_{12} & m_{13} \\ m_{20} & m_{21} & m_{22} & m_{23} \\ m_{30} & m_{31} & m_{32} & m_{33} \end{bmatrix}$$

It is known that this matrix within the framework of a single, isotropic system, can be presented as follows (within one multiplying constant):

$$M = \begin{bmatrix} 1 & -N & 0 & 0 \\ -N & 1 & 0 & 0 \\ 0 & 0 & C & S \\ 0 & 0 & -S & C \end{bmatrix}$$

where $N=\cos(2\Psi)$, $S=\sin(2\Psi)\sin\Delta$ and $C=\sin(2\Psi)\cos\Delta$.

Similarly, in the case of a non-depolarising anisotropic system, it is also possible to extract the parameters of the Jones matrix from those of the Mueller matrix.

A non-depolarising system is a system that does not modify the polarisation ratio p=1 that is defined for a Stokes vector $$\begin{bmatrix} i \\ u \\ v \\ w \end{bmatrix}$$

by $p = \dfrac{\sqrt{u^2+v^2+w^2}}{1}$

A relation is then established between the parameters $\Psi$ and $\Delta$ used in the first category of simplified ellipsometric measurements mentioned above and the parameters of the Mueller matrix presented in this second category of measuring methods.

The use of the kinetic measurement of ellipsometric angles $\Psi$ and $\Delta$ for real-time control of a preparing method is known and for example described in the American patents U.S. Pat. No. 5,277,747 dated 11 Jan. 1994 and U.S. Pat. No. 5,131,752 dated 21 Jul. 1992. However, this method cannot be used outside the scope of conventional ellipsometric defined by the absence of depolarisation application or anisotropy at the object measured or controlled. In particular, it has been observed that certain systems do not allow the realisation of simplified significant ellipsometric measurements, such as those corresponding to isotropic systems exhibiting plane interfaces, characterised simply by the parameters $\Psi$ and $\Delta$.

Still, numerous methods for preparing thin layers impose taking into account light depolarisation phenomena, for example, depositing optic structures on thick transparent substrates (glass, polymers) inducing cohesion losses. The current micro-electronic circuits exhibit systematically anisotropic patterns at submicronic scale and induce diffraction (comparable with a grid) and depolarisation (surface roughnesses in the order of the wavelength) phenomena.

The extension of the conventional ellipsometric methods for controlling micro-electronic engraving processes has been attempted, predominantly empirically, without taking into account diffraction and depolarisation phenomena (European patent 0,653,621.A1; S. Vallon et al., J. Vac. Sci. Technol. A15, 1997, p. 865; H. L. MAYNARD et al, J. Vac. Sci. Technol. B 15, 1997, p. 109). Such methods, even if they may prove satisfactory in very particular cases, can never be generalised. Moreover, they often aim at identifying the end of an attack using sudden variation of ellipsometric angles (linked with the apparition of an underlying layer). Such signatures cannot be generalised to other engraving methods. In particular, such empirical methods are not usable in the case of homogeneous engraving methods that do not give rise to the apparition of underlying layers. It is for example the case when manufacturing isolating wafers between transistors.

SUMMARY OF THE INVENTION

The purpose of the invention is to suggest a method of and a device for controlling the manufacture of a thin-layered component applicable in situations where conventional ellipsometric measurements are not possible.

The invention concerns therefore a method of and device for controlling the manufacture of a thin-layered component in which:

the object represented by its Mueller matrix is measured ellipsometrically, the manufacture is controlled in real-time in relation to the ellipsometric measurement.

According to the invention, certain parameters at least, linked with the Mueller matrix, are determined, adapted to the characterisation of the manufacture, and only these parameters are extracted from the ellipsometric measurement. These parameters, suited to the characterisation of the manufacture, are at least two different parameters from the ellipsometric angles $\Psi$ and $\Delta$ and from the trigonometric functions of the said.

Indeed, it has been contemplated and verified that even when conventional ellipsometry is not applicable since the measurements of the angles $\Psi$ and $\Delta$ lead to inaccuracies and do not enable monitoring a control method of the manufacture of a particular object, it remains possible to determine certain parameters linked with the Mueller matrix, that can be used to characterise the manufacture.

To this end, according to the invention, the set of parameters of the Mueller matrix can be used to control the manufacture.

In other cases, the manufacturing method will be studied first of all while measuring the set of parameters of the Mueller matrix using a Mueller ellipsometer. The set of results thus obtained enables extracting certain parameters from this matrix that can be either directly coefficients of the said matrix or combinations of these coefficients that are suited to the characterisation of the manufacture, fewer in number than the coefficients of the matrix properly speaking and more readily accessible than the set of these coefficients of the Mueller matrix. Once these parameters have been determined, only they can be employed for characterisation of the manufacture in its current use.

The determination of these parameters can also result from the operators' know-how, without having to resort to prior measurement of the set of coefficients of the Mueller matrix.

In different preferred embodiments, the method of the invention exhibits the following characteristics each with their own particular advantages and liable to be used according to numerous technically possible combinations:

the manufacture is made by gas dissociation and is controlled by a gas panel;

the object is anisotropic and/or depolarising;

the parameters suited to the characterisation of the manufacture are a linear combination of the lines of the Mueller matrix;

the parameters suited to the characterisation of the manufacture are a linear combination of the columns of the Mueller matrix;

the object manufactured is a solid-state component;

the deposit of a layer is controlled;

the engraving of a layer is controlled;

the composition of the layer is controlled;

the thickness of the layer is controlled;

the gas panel supplies a plasma reactor;

the gas panel controls gas flow-rates;

the gases whose flow-rates are controlled are part of the set composed of nitrogen $N_2$, ammoniac $NH_3$, hydrogen $H_2$, methane $CH_4$, helium He, silane $SiH_4$, oxygen $O_2$, nitrogen oxide $N_2O$.

The invention also concerns an Installation enabling implementation of these various methods.

Preferably, this installation comprises:

a coupled modulator at input and/or polarimeter at output.

BRIEF DESCRIPTION OF THE DRAWINGS

The invention will be described thereunder more in detail, with reference to the drawings on which.

DESCRIPTION OF THE PREFERRED EMBODIMENTS

A first embodiment of the invention relates to the control of an anisotropic system without any depolarisation.

The effect of the sample is then represented by a Jones matrix of the form:

$$\begin{bmatrix} R_P & R_{ps} \\ R_{sp} & R_s \end{bmatrix}$$

The conventional phase modulation ellipsometry can then be implemented. It is known that the measured value in the presence of a modulator (generally photo-elastic) causing a phase-shift δ(t) is:

$$I = I_o + I_c \cos \delta(t) + I_s \sin \delta(t)$$

With $\delta(t) = a \sin \omega t$ in the first order
And $$R_p/R_s = \tan \psi e^{i\Delta}, \quad R_{sp}/R_s = \tan \Psi e^{i\Delta'}, \quad R_{ps}/R_s = \tan \psi e^{i\Delta''},$$

We therefore obtain:
With A=90°, $M_o$=0°

$$I_o = 1 + \tan^2 \psi''$$
$$I_c = 2 \tan \psi'' \cos \Delta''$$
$$I_s = 2 \tan \psi'' \sin \Delta''$$

With A=90°, $M_o$=90°

$$I_o = 1 + \tan^2 \psi''$$
$$I_c = -2 \tan \psi'' \cos \Delta''$$
$$I_s = -2 \tan \psi'' \sin \Delta''$$

With A=0°, $M_o$=0°

$$I_o = \tan^2 \psi + \tan^2 \psi'$$
$$I_c = 2 \tan \psi' \tan \psi \cos \Delta'$$
$$I_s = 2 \tan \psi' \tan \psi \sin \Delta'$$

With A=0°, $M_o$=90°

$$I_o = \tan^2 \Psi + \tan^2 \psi'$$
$$I_o = -2 \tan \psi' \tan \psi \cos \Delta'$$
$$I_s = -2 \tan \psi' \tan \psi \sin \Delta'$$

A and Mo represent respectively the orientations of the analyser and of the modulator with respect to the plane of incidence.

These coefficients can be measured with a fixed wavelength or with several wavelengths. The control is made in real-time while comparing the paths of the parameters or combinations of parameters measured at set values that have been previously recorded or simulated using theoretical patterns.

Figure 1:
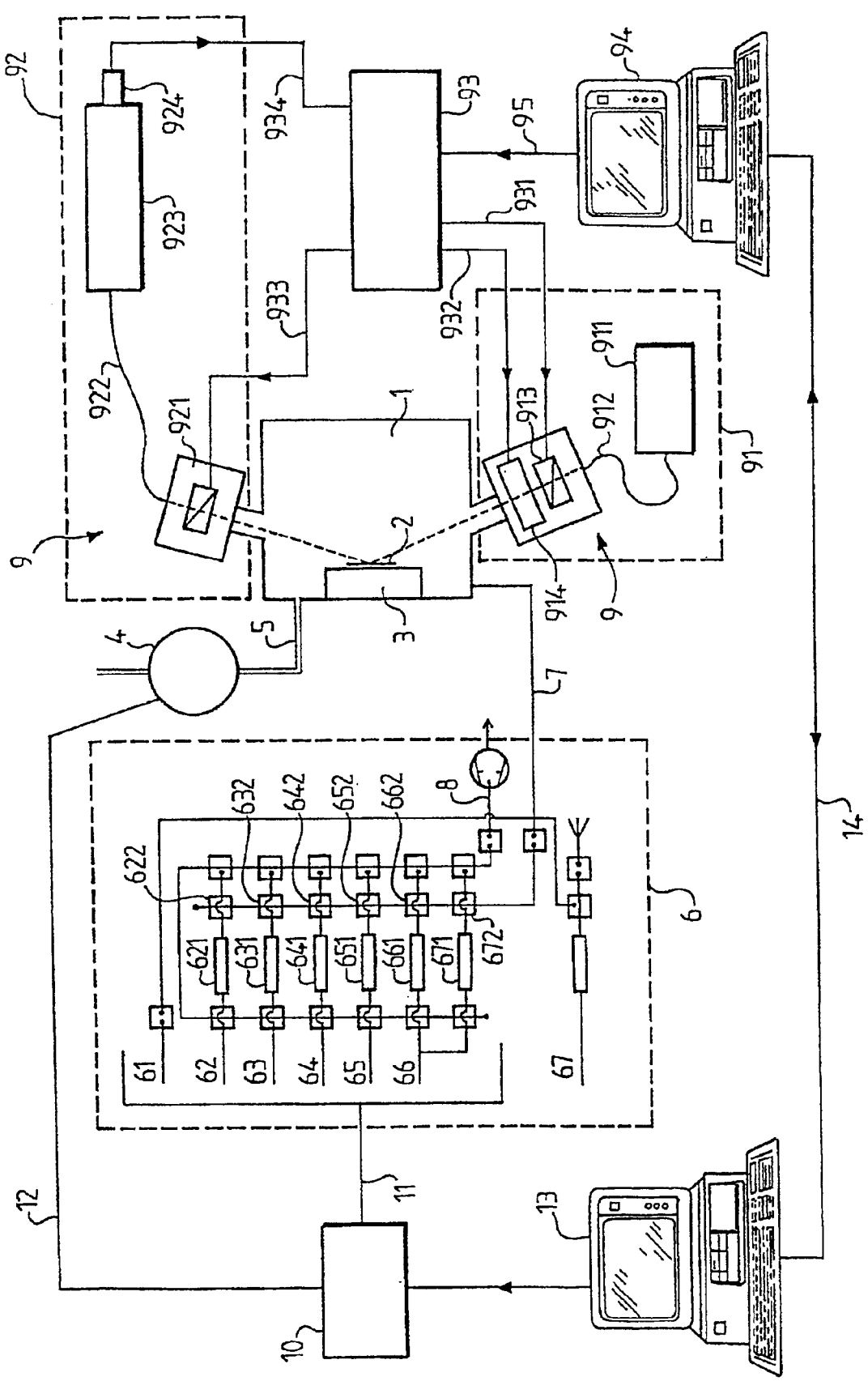
FIG. 1 is a simplified representation of a manufacturing installation that implements the invention. It comprises a plasma reactor, a gas injection system and a phase modulation ellipsometer.

In this first embodiment, measuring the system can be conducted from a phase modulation ellipsometer represented on FIG. 1. It comprises a phase modulator (input arm) and a polariser (output arm). It is thus suggested to realise real-time control of a method of preparing thin layers (by depositing or engraving) from the kinetic measurement of components of the Mueller matrix of the system or of combinations or functions of these elements. It also enables characterisation of a non-depolarising anisotropic medium according to the method described above.

A second embodiment of the invention considers the control of a depolarising system. Representing the system by a Jones matrix is then insufficient, and resorting to the Mueller matrix proves necessary.

When implementing the second embodiment, with the difference of a 'conventional' phase modulation ellipsometer comprising a single phase modulator at input and an analyser at output, the ellipsometer comprises a polarisation state generator at input and/or a polarimeter at output.

Figure 2:
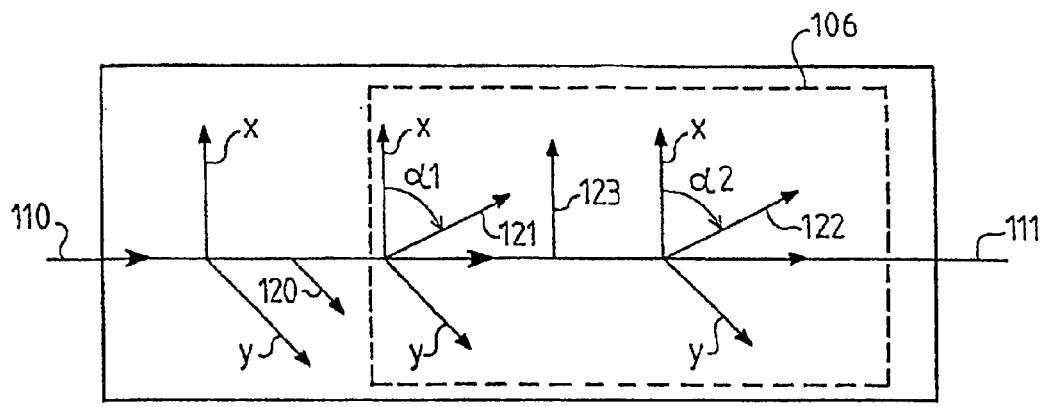
FIG. 2 is a schematic representation of an input arm that can be used in certain embodiments of the invention.

The input arm of the ellipsometer is represented schematically on FIG. 2. It comprises a linear polariser 120 and a couple modulator 106 containing two phase modulators 121 and 122 and a coupling system 123 of the phase-shift and partial polariser type. Both phase modulators 121 and 122 have the same orientation and the coupling system 123 is interposed between them and transmits the incident beam 110 from the first phase modulator 121 to the second phase modulator 122.

Preferably, the orientations of the various elements are as follows. The incident beam 110 having a given direction and a given propagation direction and whereas an incident plane is defined on the basis of this propagation direction and of the sample 2, an orthonormal system comprising a first axis x perpendicular to the propagation direction and on the plane of incidence, a second axis y perpendicular to the plane of incidence and a third axis parallel to the propagation direction and oriented in the same direction, whereby this system is direct. The polariser 120 is then a perfect polariser oriented along the axis y. Both phase modulators 121 and 122 are identical and oriented on the plane x-y along directions forming respectively with the axis y, angles α1 and α2. The angles α1 and α2 are advantageously identical and preferably equal to π/4. The coupling system 123 is oriented along the axis x In operation, the incident beam 110 is polarised linearly by the polariser 120, than undergoes double coupled modulation further to phase modulators 121, 122 and to the coupling system 123. The coupling system 123 fulfils two functions: partial polarisation (imperfect polariser) and phase-shift, which modulate the four components of the Stokes S vector.

Figure 3:
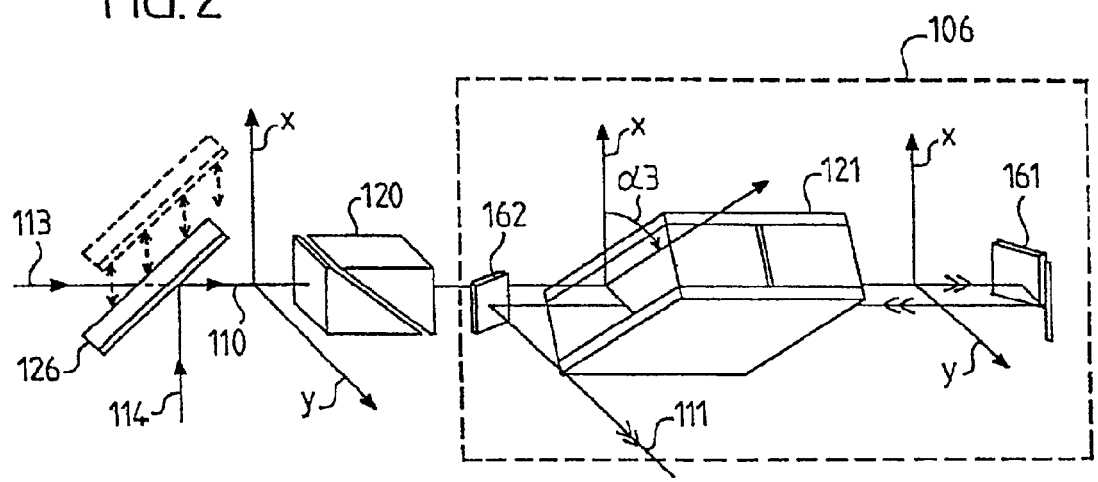
FIG. 3 shows the concretisation of an input arm of FIG. 2.

According to a particular embodiment of this input arm, represented on FIG. 3, a polariser 120 as that marketed under the name Glan Thomson polariser for linear polarisation of the incident beam 110 and coupled modulator 106 comprising a single phase modulator 121, and a coupling system 161 of the phase-shifter and partial polariser type operating in reflection. The phase modulator 121 is interposed between the polariser 120 and the coupling system 161, so that it produces a first modulation of the polarised incident beam 110 and sends it to the coupling system 161, whereas the latter returns the incident beam 110 to the phase modulator 121 that produces a second modulation. The coupled modulator 106 also comprises a mirror 162 provided between the polariser 120 and the modulator 121 that reflects the modulated beam 111 twice toward the sample.

Thus, the polariser 120 is oriented along an axis y and the modulator 121 is oriented on a plane x-y along a direction forming an angle α3 with the axis x, whereas α3 is equal to 45°. The coupling system 161 is, for its own part, oriented along the axis x, in order to enable return of the incident beam 110 parallel to the outward path. The mirror 162 returns advantageously the beam 111 along the axis y perpendicular to x.

The modulator 121 is advantageously an electro-optic modulator (Pockels cell). Such a modulator 121 enables external control of the phase-shift and allows for a pass-band in excess of 100 MHz.

The phase modulator 121 can also be a photo-elastic modulator, there is then an enhanced range of wavelengths and a wide optic window.

Advantageously, the luminous source transmits laser beams 113, 114 at several wavelengths. The ellipsometer then comprises a mobile mirror 126 enabling selection of the desired wavelength.

Figure 4:
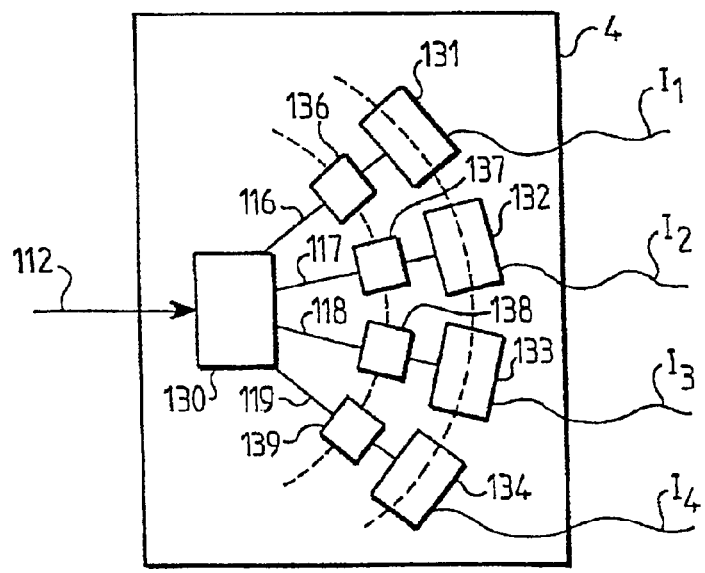
FIG. 4.represents an output arm that can be used in certain embodiments of the invention.

The output arm represented on FIG. 4 comprises advantageously a beam separator 130 that separates the measuring beam into at least four secondary beams 116–119. It also comprises polarisation analysers 136–139 conferring each of these secondary beams 116–119, a distinct polarisation state and photodetectors 131–134 that detect respectively the intensities I1 to I4 of the secondary beams 116–119. For exemplification purposes, as the secondary beams 116–119 are four in number, the related polarisation analysers 136–139 are respectively equal to zero, a 90° linear polariser, a −45° linear polariser and the association of a 45° quarter length blade and a 90° polariser.

This Mueller ellipsometer enables to control methods according to the invention. However, as stated above, numerous methods can be controlled with a simplified ellipsometric, so-called intermediate, assembly. Thus, a coupled modulator can be used in the input arm and still a single phase modulator at input and a polarimeter at output, whereas each of these configurations enables measuring more than two coefficients linked with the Mueller matrix.

It is then suggested to control in real-time a method of preparing thin layers (deposit or engraving) on the basis of kinetic measurement of combinations or functions of these elements, other than both 'conventional' ellipsometric angles ψ and Δ(or of combinations or trigonometric functions of the said angles).

In this second embodiment, while using the intermediate configurations, the following measurements can be obtained:

with only a coupled modulator at input, i.e. while measuring directly the energy of the luminous flux reflected by the sample, the coefficients of the first line of the Mueller matrix M can be provided;

with a coupled modulator at input and an analyser at output, linear combinations of the lines of the Mueller matrix M can be obtained, for instance, the sum of the first two lines when the analyser is oriented under the angle A=0 and the sum of the first and of the third lines when its orientation is A=45°;

with a single modulator at input and a polarimeter at output, there are linear combinations of the columns of the Mueller matrix M depending on the orientation of the input modulator.

In the second embodiment of the invention, a conventional phase modulation ellipsometer can be used, to allow simultaneous measurement of both elements of the Mueller matrix as follows: measuring the standardised Mueller matrix ($m_{00}=1$, the other 15 parameters of the matrix are unknown) by conventional ellipsometry (it can be suggested everywhere that the orientation of the polariser is P=45°), the following results can be provided:

1. In the conventional configuration Polariser-Modulator-Sample-Analyser (AMSP), the first three lines of the matrix (hence 12−1=11 parameters) can be measured, while combining the orientations of the modulator $M_o=0°$ (or $M_o=90°$) with the four orientations of the analyser (A=0°, 90°, 45°,−45°) on the one hand and $M_o=45°$(or −45°) on the other. That makes a total of eight measuring configurations (each configuration provides with two measured quantities).

2. While reverting the propagation direction of light, which corresponds to quite numerous current realisations of ellipsometers (Polariser-Sample-Modulator-Analyser), we have the configuration ASMP in which it is possible to measure the transpose of the matrix M, i.e. the first three columns (11 elements) using the same number of measuring configurations (8). However, if measurements were already conducted in 1., 4 additional configurations (and not eight any longer) should be sufficient, for example $M_o=0°$ (or 90°) to complete the matrix up to 14 measured elements. In conclusion, all the elements but one can be measured (14 in total) of the standardised matrix M while going through 12 configurations and reverting once the direction of the beam (of course, if reflectivity could be measured as well, the matrix may not have been standardised and thus 15 of the 16 elements could have been determined, but there will always be one missing element m33). Overdetermination of the parameters (24 quantities measured for 14 elements) can be used to build averages.

The preparing methods covered here are essentially plasma deposit of thin layers and of multilayered structures or structures with composition gradients (optic fibres). or engraving (plasma) of micro-electronic components. More generally, the control method suggested may be applied to other preparation methods using gases or metallorganic compounds (CVD: Chemical Vapour Deposition and MOCVD) or be generalised to methods based on the use of solid targets or sources (cathodic spray, vacuum evaporation, molecular jet epitaxy . . . ). In the latter case, counter-reaction on the basis of ellipsometric measurements is not conducted on a gas management, but on other control parameters (currents, temperature . . . ).

The manufacturing installation comprises a plasma chamber 1 in which the substrate 2 is placed, which is for instance, the original element of the solid-state wafer to be manufactured. This substrate is fixed to a support 3. The pressure inside the plasma chamber 1 is obtained by the effect of the pump 4, connected to the said chamber via the ductwork 5. The gas panel 6 supplies the. plasma chamber 1 via the ductwork 7. It is connected to gas supplies, respectively carrying 61 nitrogen $N_2$, 62 ammoniac $NH_3$, 63 hydrogen $H_2$, 64 methane $CH_4$, 65 helium He, 66 silane SiH4, 67 oxygen $O_2$ or nitrogen oxide $N_2O$.

The inputs 62 to 65 are each connected to the ductwork 7 via a flow-meter 621, 631, 641, 651 and a valve 622, 632, 642, 652.

Silane supply 68 is connected to two flow-meters 661 and 671 and two valves 662 and 672.

Discharge 8 towards the sewerage enables ensuring correct operation of this gas panel.

The preparation of the layers on the substrate 2 in the plasma chamber 1 is controlled using an ellipsometer 9 consisting of a transmission head 91 and of a receiving assembly 92.

The transmission head 91 comprises a source 911 connected to an optic fibre 912 with an assembly consisting of a polariser 913 and a phase modulator 914.

The receiving assembly 92 comprises a polariser-analyser 921 connected by an optic fibre 922 to a monochromator 923 followed by a photodetector 924.

The ellipsometer 9 is controlled by a processing unit 93 driven by a computer 94.

The processing unit 93 controls the polariser 913 and the modulator 914, respectively by the electric connections 931 and 932, and receives the signal of the detector 924 by the electric connection 934. Its connection with the computer 94 is ensured by the electric connection 95.

The gas panel 6 is controlled by a processing unit 10 to which it is linked by the connections 11. This processing unit 10. also controls the pump 4 and/or the power of the plasma generator via the link 12. It is controlled by a microcomputer 13 that is connected itself to the microcomputer 94 by a link 14.

Thus, the ellipsometer 9 enables to obtain, via the processing unit 93 and the microcomputer 94, the physical and chemical characteristics of the layer being deposited on the substrate 2. This information is compared with the characteristics of the product to be manufactured (and possibly with their time-related variation), characteristics that have been stored in the computer 94.

The result of this comparison controls, via the connection 14, the instructions supplied by the computer 13 to the processing unit 10 that determines the nature and the concentration of the gases inserted by the gas panel 6 into the plasma chamber 2.

The manufacturing process and therefore optimisation of the products so manufactured, are fully controlled.

As stated above, measuring the parameters $\psi$ and $\Delta$, traditionally available thanks to simplified ellipsometric measurements, often proves insufficient and ill-suited, so that It has often been necessary to provide, in the devices of the previous art, on. the substrate 2, a location that is especially dedicated to control measurements and that is lost for manufacture.

The processing unit 93 and the computer 94 are programmed so that controlling the properties of the layer deposited on the sample 2 can be realised by a small number of parameters determined previously.

What is claimed is:

1. A method of controlling manufacture of anisotropic objects and controlling manufacture of depolarizing objects, comprising the sequential steps of:
    determining at least two selected components of the Mueller matrix that represents the object and that characterizes the manufacture of the object, the selected components being other than ellipsometric angles $\psi$ and $\Delta$ and the trigonometric functions of the ellipsometric angles $\psi$ and $\Delta$;
    making an ellipsometric measurement of object during manufacture;
    extracting, from the ellipsometric measurement, only the determined selected components of the Mueller matrix; and
    controlling the manufacture of the object in relation to the extracted components of the Mueller matrix,
    the at least two selected components being one of a linear combination of the lines of the Mueller matrix and a linear combination of the columns of the Mueller matrix.

2. A control method according to claim 1, characterised in that the said object is anisotropic.

3. A control method according to claim 1, characterised in that the said object is depolarising.

4. A control method according to claim 1, characterised in that the said object induces diffraction phenomena.

5. A method for controlling the manufacture of an object according to claim 1, characterised in that the object manufactured is a solid-state component.

6. A method for controlling the manufacture of an object according to claim 5, characterised in that the ellipsometric measurement characterizes a layer during deposit.

7. A method for controlling the manufacture of an object according to claim 5, characterised in that the ellipsometric measurement characterises a layer during engraving.

8. A method for controlling the manufacture of an object according to claim 6, characterised in that the ellipsometric measurement characterises the composition of the layer.

9. A method for controlling the manufacture of an object according to claim 6, characterised in that the ellipsometric measurement characterises the thickness of the layer.

10. A control method according to claim 1, characterised in that the manufacture is carried out by gas dissociation and it is controlled by a gas panel.

11. A method for controlling the manufacture of, an object according to claim 2, characterised in that the gas panel supplies a plasma reactor.

12. A method for controlling the manufacture of an object according to claim 2, characterised in that the gas panel controls gas flow-rates.

13. An installation for making anisotropic objects and making depolarizing objects, comprising:
    an ellipsometer configured to make an ellipsometric measurement of an object during manufacture;
    a processor configured to extract, from the ellipsometric measurement, only determined selected components of the Mueller matrix that represents the object and that characterizes the manufacture of the object,
    the processor also configured to control the manufacture of the object in relation to the extracted components of the Mueller matrix, wherein,
    the determined selected components are at least two selected components of the Mueller matrix that characterize the manufacture of the object, and
    the determined selected components are other than ellipsometric angles $\psi$ and $\Delta$ and trigonometric functions of the ellipsometric angles $\psi$ and $\Delta$,
    the at least two selected components being one of a linear combination of the lines of the Mueller matrix and a linear combination of the columns of the Mueller matrix.

14. An installation for manufacturing an object according to claim 13, characterised in that it is conducted by gas dissociation.

15. An installation for manufacturing an object to claim 13, characterised in that it comprises a coupled modulator at input.

16. An installation for manufacturing an object to claim 13, characterised in that it comprises a polarimeter at output.

17. The installation of claim 13, further comprising:
    a plasma chamber (1) with power control;
    a support (3) within the chamber for supporting the object, the object being a substrate (2) serving as an original element of a solid-state wafer to be manufactured;
    a pump (4) connected to the chamber to maintain a pressure within the chamber; and
    a gas panel (6) connected to the chamber to supply the chamber with gas, the gas panel having plural gas inputs (62–65), each gas input connected to the chamber via a flow-meter (621, 631, 641, 651) and a valve (622, 632, 642, 652),
    the ellipsometer (9) comprising a transmission head (91) and a receiving assembly (92), the ellipsometer arranged to control the gas panel to control a preparation of layers on the substrate,
    the transmission head comprising a polarization state generator,
    the receiving assembly comprising a polarimeter,
    the processor comprising a first processing unit and a second processing unit,
    the first processing unit (93) connected to the transmission head to control the polarization state generator, and connected to the receiving assembly to receive an output signal from the polarimeter, and
    the second processing unit connected to the first processing unit for receiving control signals from the first processing unit, and connected to the gas panel, the pump, and the power control of the chamber.

18. A manufacturing installation, comprising:

a plasma chamber (1) with power control;

a support (3) within the chamber for supporting a substrate (2) serving as an original element of a solid-state wafer to be manufactured;

a pump (4) connected to the chamber to maintain a pressure within the chamber;

a gas panel (6) connected to the chamber to supply the chamber with gas, the gas panel having plural gas inputs (62–65), each gas input connected to the chamber via a flow-meter (621, 631, 641, 651) and a valve (622, 632, 642, 652);

an ellipsometer (9) comprising a transmission head (91) and a receiving assembly (92), the ellipsometer arranged to control the gas panel to control a preparation of layers on the substrate based on ellipsometric measurement of the substrate, the transmission head comprising a phase modulator, the receiving assembly comprising a polarizer-analyzer;

a first processing unit (93) connected to the transmission head to control the phase modulator, and connected to the receiving assembly to receive an output signal from the polarizer-analyzer, the first processing unit configured to extract, from the ellipsometric measurement, only determined selected components of the Mueller matrix describing the substrate and to control the manufacture of the substrate in relation to the extracted components of the Mueller matrix, a second processing unit connected to the first processing unit for receiving control signals from the first processing unit, and connected to the gas panel, the pump, and the power control of the chamber, wherein, the determined selected components are at least two selected components of the Mueller matrix that characterize the manufacture of the object, the selected components being other than ellipsometric angles $\psi$ and $\Delta$ and trigonometric functions of the ellipsometric angles $\psi$ and $\Delta$, the two selected components being one of a linear combination of the lines of the Mueller matrix and a linear combination of the columns of the Mueller matrix.

* * * * *